United States Patent
Sperling et al.

(10) Patent No.: US 7,679,756 B2
(45) Date of Patent: *Mar. 16, 2010

(54) DEVICE FOR A GONIOMETRIC EXAMINATION OF OPTICAL PROPERTIES OF SURFACES

(75) Inventors: Uwe Sperling, Geretsried (DE); Peter Schwarz, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 7 days.

This patent is subject to a terminal disclaimer.

(21) Appl. No.: 11/187,694

(22) Filed: Jul. 22, 2005

(65) Prior Publication Data

US 2006/0033922 A1 Feb. 16, 2006

(30) Foreign Application Priority Data

Jul. 28, 2004 (DE) .................. 20 2004 011 811

(51) Int. Cl.
*G01B 11/30* (2006.01)
(52) U.S. Cl. ...................... 356/600; 356/446
(58) Field of Classification Search ............. 356/446, 356/236; 250/228
See application file for complete search history.

(56) References Cited

U.S. PATENT DOCUMENTS

| | | | | |
|---|---|---|---|---|
| 3,999,864 A * | 12/1976 | Mutter | ............... | 356/448 |
| 4,479,718 A * | 10/1984 | Alman | ............... | 356/405 |
| 4,583,858 A * | 4/1986 | Lebling et al. | ............... | 356/446 |
| 4,917,495 A * | 4/1990 | Steenhoek | ............... | 356/446 |
| 5,387,977 A * | 2/1995 | Berg et al. | ............... | 356/407 |
| 5,583,642 A * | 12/1996 | Nakazono | ............... | 356/405 |
| H1655 H * | 6/1997 | Task | ............... | 356/446 |
| 6,018,396 A * | 1/2000 | Rapaport et al. | ............... | 356/446 |
| 6,473,165 B1 * | 10/2002 | Coombs et al. | ............... | 356/71 |
| 7,034,931 B2 * | 4/2006 | Jones et al. | ............... | 356/237.2 |
| 7,068,363 B2 * | 6/2006 | Bevis et al. | ............... | 356/237.5 |
| 7,276,719 B2 * | 10/2007 | Schwarz | ............... | 356/237.1 |
| 7,433,055 B2 * | 10/2008 | Schwarz et al. | ............... | 356/446 |
| 2005/0018195 A1* | 1/2005 | Lex | ............... | 356/446 |

* cited by examiner

*Primary Examiner*—Gregory J Toatley, Jr.
*Assistant Examiner*—Juan D Valentin
(74) *Attorney, Agent, or Firm*—Greer, Burns & Crain, Ltd.

(57) ABSTRACT

A device for examining the optical properties of surfaces includes at least one first radiation device emitting radiation to a surface to be examined at least at a first predetermined spatial angle, at least one first detector for capturing the radiation emitted to and reflected back from the surface, wherein the detector, allowing a local resolution of detected radiation, is positioned at least at a second predetermined spatial angle relative to the surface. At least one spatial angle at which the radiation device and/or the detector are positioned, is variable and the radiation device and the detector are positioned in a space at least part of which exhibits light-reflecting properties.

39 Claims, 5 Drawing Sheets

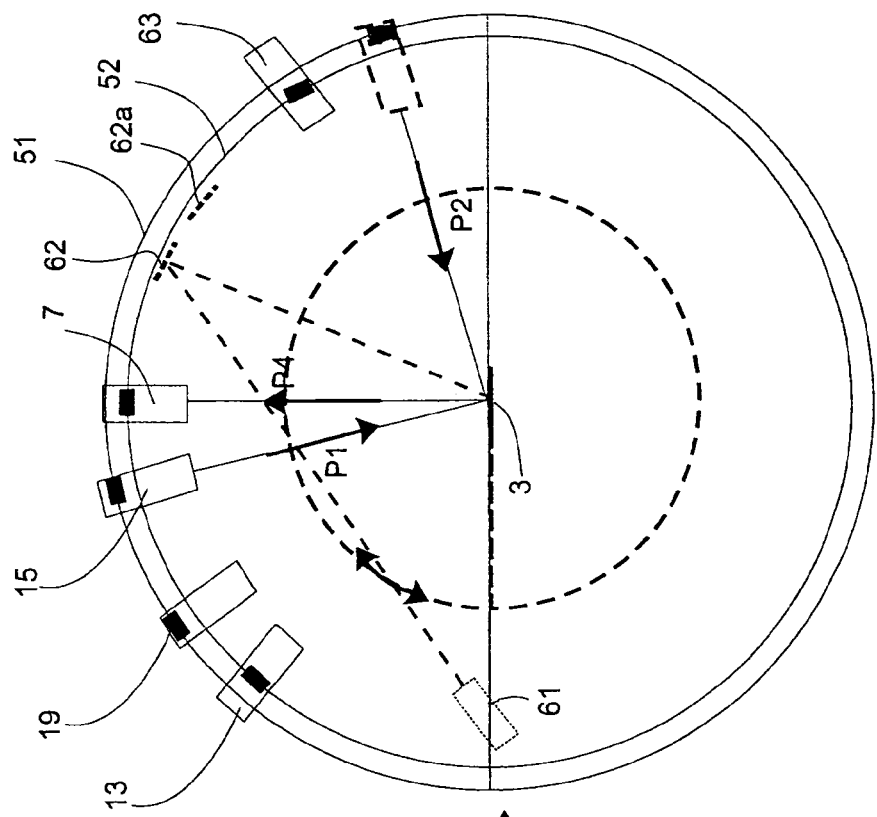
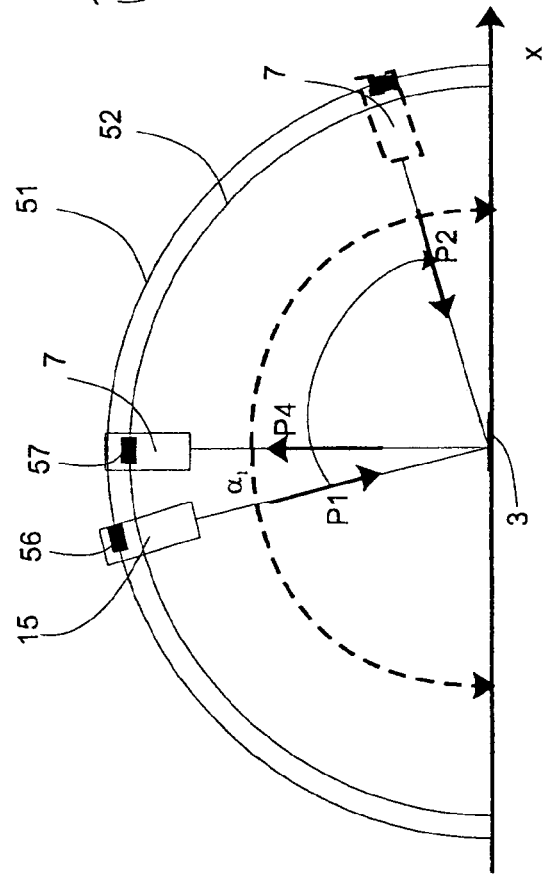
Fig.2
Fig. 1

DEVICE FOR A GONIOMETRIC EXAMINATION OF OPTICAL PROPERTIES OF SURFACES

BACKGROUND

The present invention relates to a device for a goniometric examination of the optical properties of surfaces. The device will be described below with reference to examining car bodywork. However, reference is made to the fact that the device of the invention may also be applied to examining other kinds of surfaces.

Such devices for a goniometric examination of the optical properties of surfaces are known from the prior art. Generally, these use a light source which emits light to the surface to be examined and a detector that detects and evaluates the light reflected or diffused off said surface. Such evaluation allows a determination of the optical properties of surfaces such as color or gloss. Such determination or characterization is required since motor-vehicle bodies or their paintwork make different impressions on the human eye depending on the incident light, thus requiring a neutral characterization.

Lately finishes have been gaining popularity which comprise in particular pigments or so-called flakes. These pigments or flakes are for instance metal particles statistically distributed in the layer of finish or its surface. More precisely, metal pigments may consist of very thin metal flakes acting as miniature reflectors. Standardizing these types of finishes or measuring the properties of their surfaces creates problems since, depending on the incidence angle of the light, said pigments exhibit different characteristics and for example the slightest variation of the viewing angle may already result in a different color or a different brightness.

Among other things manufacturers also use finishes having interference pigments which, in particular in viewing large surface areas, result in color blending at more or less precisely specified color alteration angles (Flop) which may lead to largely different color perceptions which in turn leads to varying overall impressions of the brightness or color of the finished surfaces.

These effects and different perceptions of surfaces caused for example by different densities, distribution and compositions of finish additives such as flakes or ornamental pigments cannot be detected with prior art devices since those detectors only supply information on the composite intensity of the incident light from various positions on the measuring surface i.e. they integrate intensity without local resolution.

It is the object of the present invention to allow on the one hand, a resolution of changes caused by shifting views of finished surfaces for example at slightly different spatial angles while on the other hand also allowing a viewing at largely deviating angles.

SUMMARY OF THE INVENTION

The device of the present invention for examining the optical properties of surfaces comprises at least one first radiation means which emits radiation to the surface to be examined at least at a first predetermined spatial angle. In addition at least one first detector means is provided for capturing the radiation emitted to and reflected back from the surface wherein said detector means, allowing a local resolution of the detected radiation, is positioned at least at one second predetermined spatial angle relative to the surface to be examined.

Therein at least one spatial angle at which said radiation means and/or said detector means are positioned, is variable. According to the invention the radiation means and the detector means are positioned in a space at least part of which exhibits light- or radiation-reflecting properties.

A space is understood to mean a substantially closed volume component. Preferably this is the space substantially placed above the surface to be examined.

A space having light-reflecting properties is understood to mean that said space exhibits light-reflecting properties at least in one section, preferably a section at the inner surface. Preferably substantially the entire inner surface of said space, i.e. the surface facing towards the surface to be examined, exhibits light-reflecting properties. Said space is preferably an integrating sphere or an integrating sphere segment, also referred to as an Ulbricht sphere. Preferably the portion of the space that is positioned substantially parallel to the surface to be examined, also exhibits light- or radiation-reflecting properties.

Positioning the radiation or detector means in the space is understood to mean that the means themselves do not necessarily have to be inside said space but in any case the radiation means directs radiation into said space and the detector means detects radiation emitting from said space. The means may for example be positioned above the space and apertures arranged in the space through which the radiation from the radiation means passes into said space or, exiting from said space, passes to the detector means.

In this way it can be achieved that non-collimated or non-directional light is generated under predetermined conditions such that the surface properties can be characterized under illumination with substantially diffused light. Extensive tests have shown that this way of generating non-directional light will not significantly falsify measuring results achieved in measuring with directional radiation, such that a combination of different measuring methods is feasible.

Radiation means is understood to mean a radiation source or a light source, in particular but not exclusively in the shape of light-emitting diodes and/or laser diodes, light bulbs, halogen light bulbs and the like. A configuration of a number of light sources such as a number of light-emitting diodes having different emission spectra is also understood to mean a radiation means.

A spatial angle is understood to mean within the scope of the present invention, as distinguished from the mathematical concept of a spatial angle, a tuple of spatial subangles. Herein the first component of the spatial angle, i.e. the first spatial subangle $\alpha$, refers to the projection angle to the x-/z plane relative to the positive z axis of a direction in space defined by a half straight line beginning in the point of origin in a Cartesian coordinate system.

Furthermore, the second component of the spatial angle, i.e. the second spatial subangle $\beta$, refers to the projection angle of said half straight line to the y-/z plane relative to the positive z axis. The coordinate system is oriented such that the measuring surface or at least portions of the measuring surface lie on the x-/y plane.

The spatial angle is thus suitable for clearly characterizing the orientation of the radiation or detector means relative to the surface to be examined. The geometrical orientation of the spatial angles will be illustrated again in the description of the figures. A spatial angle of (0°, 0°) is understood to mean a spatial angle where the radiation or detector means is positioned above the surface to be examined such that the radiation emitting for example from the radiation means is incident on the surface to be examined substantially perpendicularly.

A detector means is understood to be any means capable of detecting at least one parameter of incident light and emitting a signal corresponding to said parameter. Detector means is intended to include both photo sensors, photo cells, photo detectors, and also for example cameras, CCD chips and the like.

A variable angle of a device is understood to mean that the device is for example not mechanically fixed but it can be varied by external measures such as motor-aided shifting on a curved rail, displaceable or rotatable supports and the like.

It is also conceivable that only one spatial subangle of either the radiation means or the detector means is changed and the other of the spatial subangles remains unchanged.

Preferably the first detector means comprises a preferably plane image-capturing component which allows a local resolution of detected radiation. Said plane component may for example be a CCD chip capable of examining incident radiation with local resolution. Said examination with local resolution allows examining the effects—in particular spectral effects—generated by the individual pigments or flakes.

In contrast to this, a plane detector without local resolution would, by integration of the intensity of radiation incident on each individual point on the detector surface, only determine the composite intensity of the incident radiation and thus would not provide information on the origins.

In order to achieve that examination also takes into account effects caused by differing incident light or incident light at different spatial angles it is also conceivable to provide a number of light sources radiating onto the surface at different spatial angles. However it is also conceivable to position a radiation means initially at a first predetermined spatial angle, then perform a measurement of light incident on the surface, and then change said spatial angle so as to perform another measurement.

It is furthermore possible to characterize the effects by providing instead of a number of radiation means, a number of detector means which allow detection at different spatial angles. It is also alternatively possible and proposed in the invention to position the detector means initially at a first predetermined spatial angle, then perform a measurement and then shift said spatial angle in further steps so as to perform one or more other measurements.

Furthermore it is also possible to provide a combination, i.e. a number of radiation means and a number of detector means. Additionally it is also conceivable to vary while measuring both the spatial angle at which the radiation means is positioned and the spatial angle at which the detector means is positioned.

Further a number of radiation and detector means may be provided whose spatial angles are variable at least in part.

Preferably the first spatial subangle at which said first radiation means is positioned relative to the surface to be examined, is variable. Another preferred embodiment provides that the first spatial subangle of the first detector means positioned relative to the surface to be examined, is variable.

Preferably said first and said second detector means are positioned at substantially the same second spatial subangle. A preferred embodiment provides that the first radiation means and/or the first detector means travel substantially on a semicircle above the surface to be examined.

Another preferred embodiment provides for said first spatial subangle to be variable in the range of 0° to 360°, preferably from 0° to 180°. A variation in the range of 0° to 360° allows the respective radiation and/or detector means to travel substantially completely around the surface to be examined so as to allow measuring by transmitted-light methods.

Another embodiment provides a control means for actuating at least one spatial angle for a radiation and/or detector means in a predetermined range.

It is for example possible to vary the first spatial subangle of the first radiation means at predetermined intervals, for example in 1° increments. In this way measurement can be carried out continuously, for example at predetermined intervals from 0° to 180°.

The corresponding first spatial subangle of the first detector means can be varied in the same way. It is further possible to vary the corresponding spatial angles both for the radiation means and the detector means at predetermined intervals. An optical scan can for example be carried out in such a way that the radiation means or the detector means is continuously shifted within a predetermined angular range for example from 0° to 180° or else from 0° to 360°.

The control means can further be configured such that the user can set predetermined spatial angles which are then actuated. Thus the user can for example input a predetermined pair of spatial angles $(\alpha_1; \beta_1)$ and $(\alpha_2; \beta_2)$ so as to cause the first radiation means and the first detector means to take precisely defined positions relative to the surface to be examined.

Another embodiment provides actuating the corresponding second spatial subangles $\beta_1$ and $\beta_2$. In another embodiment the control means is configured such that the first control means and the first detector means actuate preprogrammed angles consecutively so as to carry out a complete measuring cycle. The first radiation means can for example be preset for the consecutive angles $\alpha_1 = 30°, 60°, 90°, 120°, 150°$ and $170°$. Any other desired angles may of course be preprogrammed. The detector means can be programmed in a similar way.

Preferably it is also possible to change one or both spatial subangles in small increments such as 1° steps. In this way the plasticity of the ornamental pigments can be examined by means of small angle changes.

Another embodiment provides a number of radiation means and/or a number of detector means. As will be explained below, it is useful for some measuring variants to have two or more radiation means concurrently illuminate the surface. In this case it is also possible to have the control means actuate a number of radiation means and/or a number of detector means and to allow any desired angular position for each. In this way specific illuminations can be realized and/or measuring accelerated.

In another embodiment at least one radiation means and/or at least one detector means are positioned at least on one guiding device which allows changes in the position of the radiation means and/or the detector means on a predetermined path. Said guiding device may for example be a substantially circular rail on which the respective radiation means or detector means is guided substantially in a semicircle around the surface to be examined.

Said guiding device may also be an arm with the radiation or detector means positioned at its end so as to allow said detector means to be guided on a predetermined path. The configuration of said guiding devices may also be other than substantially circular.

In another preferred embodiment said at least one guiding device is configured such that the spatial angles at which the radiation means are positioned, and the spatial angles at which the detector means are positioned, can substantially be changed independently of one another. This means that the guiding device is configured such that said radiation means and said detector means can be guided past one another, for example when the radiation means at an angle $\alpha_1 = 30°$ shifts to an angle $\alpha_1 = 120°$ while the detector means shifts from a spatial angle $\alpha_2 = 120°$ to a spatial angle $\alpha_2 = 30°$.

Another preferred embodiment provides at least one more radiation means or at least one more detector means which emit radiation to the surface to be examined at least at one third predetermined spatial angle or which detect radiation emitted to and reflected back from said surface. As specified above it is essential for some measuring variants to emit radiation to the surface to be examined at two or more spatial angles concurrently. The third spatial angle is variable in a preferred embodiment.

Another device of the present invention for examining the optical properties of surfaces comprises at least one first radiation means which emits radiation to a surface to be examined at least at a first predetermined spatial angle. In addition at least one first detector means is provided for capturing the radiation emitted to and reflected back from at least a portion of the surface wherein said detector means is positioned at least at a second predetermined spatial angle relative to the surface, allowing local resolution of the detected radiation. Subsequently at least one second radiation means is provided.

The radiation means and the detector means are positioned in a space at least part of which exhibits light-reflecting properties.

Preferably said other radiation means emits directional radiation. In another preferred embodiment said other radiation means emits diffused radiation.

In another preferred embodiment said radiation means and said detector means are positioned in a common housing that is substantially opaque to radiation and comprises an opening through which radiation passes onto the surface to be examined. In this way one can assure that substantially only such light enters the individual detector means as is reflected back from the surface to be examined.

In another preferred embodiment said surface is irradiated concurrently with at least two radiation means, at least intermittently. Preferably it is therefore possible to irradiate said surface only with said first or only with said second or with both radiation means concurrently. If more than two radiation means are provided in another embodiment it is conceivable to activate only one or random combinations—or all—of said number of radiation means.

In this way different results can be obtained for the surface to be examined such as information on surface behavior with irradiation at one predetermined angle only, or further data for concurrent irradiation at a number of angles. In this way one can for example achieve an approximation to diffused daylight or a characterization of gloss.

In another preferred embodiment said second detector means is selected from a group of detector means comprising photo cells, photo elements, photo diodes and the like. As illustrated above, these elements do not permit local resolution of the examined radiation but only an examination of the radiation intensity and the spectral characteristics.

The preferred radiation means for resolving the spectral characteristics is a plurality of LCDs which substantially cover the entire spectrum of visible light. In this way a spectral resolution of the receiver means or detector means is achieved. However, it is also possible to use frequency-selective elements such as optical gratings in the ray path after the surface to be examined.

In another preferred embodiment said first detector means which allows local resolution of examined radiation also comprises means for determining the total intensity of incident radiation. This can be done in particular but not exclusively through integration of the incidence intensities on the individual photo cells of a CCD chip.

In another preferred embodiment the first detector means is positioned at a first spatial subangle of substantially 0° above the surface. Preferably said first detector means is also positioned at a second spatial subangle of 0° above the surface, meaning—as described above—that preferably it detects radiation emitting substantially perpendicularly from the surface to be examined.

In another preferred embodiment at least one radiation means is positioned at a first spatial subangle relative to the surface selected from a group of angles including −45°, −15° and +75°. Preferably said second spatial subangle is 0°.

The specified angles are to be understood as approximate values insofar as an angle for example of 45° is understood to include angles within a tolerance range of ±50°, i.e. angles between 40° and 50°.

In another preferred embodiment a plurality of radiation means is provided at predetermined spatial angles. First spatial subangles of −15, −45°, or +45° and +75° are preferably used. Otherwise it is also possible to use one radiation source and to position the respective detector means at predetermined first spatial subangles such as in particular but not exclusively −75°, −65°, −45°, −15° or 20°. Any other desired detection or incidence angles may of course be chosen. However, the magnitudes indicated refer to standards some of which are gauged. Thus far, however, no large first spatial subangles have been used in the prior art, i.e. spatial angles comparatively close to ($\alpha$=−90°) or ($\alpha$=+90°). Using such spatial subangles allows a better characterization of pigments or their distribution on the surface. Preferably at least one detector means is positioned at such a first spatial subangle whose amount is larger than (70°, $\beta_2$) and preferably larger than (75°, $\beta_2$).

Preferably said first and said second spatial angle are chosen such that a high difference relative to said first spatial subangle will result, preferably a difference of more than 100°.

In another preferred embodiment at least one detector means is positioned at a first spatial subangle whose amount is small, preferably an angle whose amount is smaller than (30°, $\beta$) and particularly preferred smaller or equal (60°, $\beta$). Using such spatial subangles allows a better characterization of pigments having a substantial color shift.

In another preferred embodiment at least one radiation means emits non-directional or diffused radiation.

Preferably said first and said second spatial angle are chosen such that a low difference relative to said first spatial subangle will result, preferably a difference of less than 50°.

Directional radiation is understood to mean such radiation where the light is incident on the surface to be examined in a substantially predetermined direction or at a predetermined spatial angle. In another preferred embodiment at least one radiation means emits directional radiation (i.e. beams having a defined or sometimes a standardized aperture).

Non-directional radiation is understood to mean radiation incident on the surface to be examined at different spatial angles, for example after multiple reflection at the interior housing surface. This can be achieved in particular but not exclusively by using diffuser or frosted-glass plates.

In another preferred embodiment a number of radiation means are substantially positioned on an arc of a circle. In another preferred embodiment it is also conceivable that a number of detector means are substantially positioned on an arc of a circle or a number of radiation and detector means are substantially positioned on an arc of a circle. In this way it is achieved that the respective radiation means and/or detector means are substantially positioned at the same second spatial subangle or in one plane.

In a preferred embodiment said second spatial subangle at which the respective radiation and detector means are positioned is substantially 0°.

Another preferred embodiment provides means which allow that both a first detector means and a second detector means can detect radiation at the same predetermined spatial angle. These means may for example be beam splitters which cause a specified portion of the radiation to reach the first detector means and another portion, the second detector means. It is preferred that said first detector means allows a locally differentiating analysis of the radiation and the second detector means a locally integral intensity examination.

Other means are also conceivable such as partly silvered reflectors, polarizers and the like.

Another preferred embodiment provides a plurality of radiation means having predetermined, substantially regular, angular distances relative to one another. Said plurality is preferably positioned at the same second spatial subangles but at different first spatial subangles. In this case the angular distance will result from the difference of said first spatial subangle of a radiation means to that of an adjacent radiation means.

In another preferred embodiment a plurality of radiation means is positioned both at different first spatial subangles and different second spatial subangles. It is likewise conceivable that a plurality of detector means are positioned at different first and/or second spatial subangles, and both a plurality of radiation means and a plurality of detector means which differ from one another in respect of their first and/or second spatial subangles.

The present invention further relates to a method for the examination of optical properties of surfaces. In a first process step, a first radiation is emitted to a surface to be examined at least at one first predetermined spatial angle $(\alpha_1; \beta_1)$.

Another process step provides that the radiation reflected back from the surface to be examined is detected by means of at least a first detector means at least at a second predetermined spatial angle $(\alpha_2; \beta_2)$ wherein said detector means allows local resolution of the detected radiation.

In another process step at least the spatial angle $(\alpha_2; \beta_2)$ at which the at least one detector means is positioned, is changed to the spatial angle $(\alpha_2'; \beta_2')$.

In another process step the radiation of said first detector means reflected back from the surface to be examined is detected at the changed second spatial angle $(\alpha_2'; \beta_2')$.

It is preferably possible to effect a number of changes of the spatial angle and a number of subsequent detections of the radiation to be examined during one measuring cycle. Preferably said changes can occur in predetermined steps—such as 1° increments or the like.

Further it is conceivable to carry out measuring not in 1° increments but continuously, meaning that a predetermined angular range, for example $20°>\alpha_2>50°$ is scanned and the light reflected back is detected continuously. In this way continuous characteristics of the surface can be captured.

Another method according to the invention provides a process step wherein the first radiation is emitted to a surface to be examined at least at one first predetermined spatial angle $(\alpha_1; \beta_1)$.

Another process step provides that the radiation reflected back from the surface to be examined is detected by means of at least a first detector means at least at a second predetermined spatial angle $(\alpha_2; \beta_2)$ wherein said detector means allows local resolution of the detected radiation.

In another process step the spatial angle $(\alpha_1; \beta_1)$ of the at least one radiation means is changed to a spatial angle $(\alpha_1'; \beta_1')$. In another process step the first radiation is directed at the surface to be examined at the changed spatial angle $(\alpha_1'; \beta_1')$.

In another process step the radiation reflected back from the surface to be examined is detected by means of said first detector means at the second predetermined spatial angle $(\alpha_2; \beta_2)$.

In this method it is also preferred to change the respective first spatial subangles $\alpha_1$ or $\alpha_2$ frequently and after changing, to detect the respective radiation. Additionally it is also conceivable to combine the above methods, i.e. to change continuously or in steps, both the spatial angle at which the radiation means is positioned relative to the surface and the spatial angle at which the detector means is positioned relative to the surface.

These changes allow the detection of any desired angular distance and substantially at every possible angle of incidence and of reflection.

Another method according to the invention provides a first process step wherein a first radiation is directed at a surface to be examined at a first predetermined spatial subangle. Another process step provides that a second radiation is directed at the surface to be examined at a third predetermined spatial angle and another process step provides that the radiation reflected back from the surface to be examined is detected by means of a first detector means at a second predetermined spatial angle wherein said detector means allows local resolution of the detected radiation.

Preferably the first radiation and the second radiation are emitted concurrently, at least intermittently.

One process step provides a first radiation emitted to a surface to be examined at a first predetermined spatial subangle. Another process step provides that the radiation reflected back from the surface to be examined is detected by means of a first detector means at a second predetermined spatial angle wherein said detector means allows local resolution of the detected radiation.

Another process step provides that the radiation reflected back from the surface to be examined is detected by means of a second detector means at a third predetermined spatial angle.

Another method according to the invention provides a first process step wherein a first radiation is directed at a surface to be examined at a first predetermined spatial subangle. Another process step provides that a second radiation is directed at the surface to be examined at a third predetermined spatial angle and another process step provides that the radiation reflected back from the surface to be examined is detected by means of a first detector means at a second predetermined spatial angle wherein said detector means allows local resolution of the detected radiation.

A change of a first predetermined spatial angle is understood to mean that at least the first or the second spatial subangle is changed. It is therefore possible to change the first spatial subangle while maintaining the second spatial subangle or to change only the second spatial subangle while maintaining the first spatial subangle. It is also possible to change both spatial subangles.

In the method of the invention the radiation means and the detector means are preferably positioned in a space at least part of which exhibits light-reflecting properties.

BRIEF DESCRIPTION OF THE DRAWINGS

Other advantages and embodiments can be taken from the accompanying drawings.

These show in:

FIG. 1 is a schematic illustration of the device of the present device;

FIG. 2 is a schematic illustration of another embodiment of the present device;

FIG. 8d is a schematic illustration of the brightness pattern shown in FIG. 8a.

DETAILED DESCRIPTION OF THE PREFERRED EMBODIMENT

Figure 7:
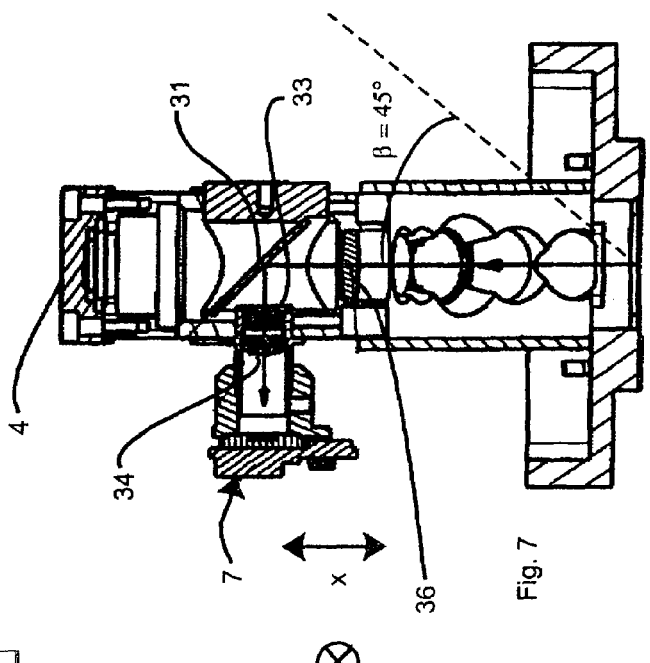
FIG. 7 is a sectional view of the device in FIG. 4.

FIG. 1 shows a schematic illustration of a device 1 of the invention. It comprises a radiation means 15 which is positioned at a predetermined spatial angle relative to a surface to be examined 3. A detector means 7 is further provided which is also positioned at a predetermined spatial angle relative to the surface to be examined 3. The arrow P1 indicates light directed at the surface 3, and arrow P4 the light reflected back from said surface 3 and thus detected by the detector means 7.

A radiation means 15 is positioned at a predetermined first spatial subangle $\alpha_1$. In the illustration the detector means 7 is positioned at a spatial subangle $\alpha_2=0°$. Respective spatial subangles $\beta_1$ and $\beta_2$ of the radiation means 15 and the detector means 7 are also 0° in the illustrated embodiment. Angles deviating therefrom would mean a rotation about the axis x, or a rotation out of the plane of the drawing.

As mentioned above, the angle $\alpha_1$ is adjustable. For this purpose the radiation means 15 travels by means of a displacement means 56 on a guide means 51 which in this embodiment is substantially configured as a semicircle. The radiation means 15 can thus cover all of the angles from (−90°; 0°) to (+90°; 0°) relative to the surface to be examined 3.

The detector means 7 is also guided by means of a displacement means 57 on a guide means 52 which is substantially circular in the present case. The detector means 7 can also travel in a range of angles from (−90°; 0°) to (+90°; 0°) relative to the surface to be examined 3.

It is preferably possible to vary the respective spatial subangle β. In this way both the radiation and the detector means could be positioned at the same angle α (but different angles β).

The positions of the guiding device 51, 52 also allows that the radiation means 15 and the detector means 7 travel past one another, i.e. both the radiation means 15 can take a smaller first spatial subangle than the detector means 7 and reversely, the detector means 7 can take a smaller first spatial subangle than the radiation means 15. For example for carrying out a measurement the radiation means 15 can first be positioned as shown in FIG. 1 and then measuring can take place at this position. Another step provides for the detector means 7 to travel into the second position indicated with interrupted lines, and radiation can again emit onto the surface 3 along the arrow P2 so as to carry out another measurement.

FIG. 2 is a schematic illustration of another embodiment of the present invention. Unlike the embodiment of FIG. 1, another detector means 13 and another radiation means 19 is provided. These radiation and detector means 19, 13 are also variable in respect of their spatial angles relative to the surface to be examined 3 which is why at least in this embodiment the guide means 51, 52 are positioned around the surface to be examined substantially in a circle, i.e. the individual radiation 15, 19 and detector means 7, 13 can rotate around the surface to be examined 3 substantially at a total angle of 360°. In this way, with the radiation means 15, 19 positioned beneath the surface to be examined 3, the transmitted light method can be applied.

Instead of the illustrated guiding devices 51, 52, individual or a number of radiation or detector means may be provided on movable arms so as to allow adjusting the angles of incidence and of detection. It is also conceivable to provide the radiation means 15, 19 in other positions—in particular in the interior of the guiding devices 51, 52—as indicated with reference numeral 61. In this case, the interior surface for example of a hemispherical housing may be equipped with reflectors 62 which direct the radiation to the surface to be examined 3.

More precisely, a plurality of reflectors 62, 62a etc. may be positioned at predetermined angles and in this case the radiation means 61 can be rotatably supported.

Reference numeral 63 refers to a detector means not allowing local resolution such as in particular but not exclusively a sensor.

Figure 3:
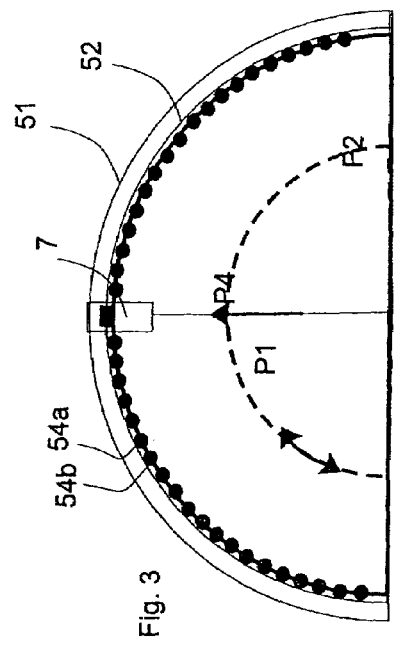
FIG. 3 is a schematic illustration of another embodiment of the present device.

FIG. 3 is an illustration of another embodiment of the device of the present invention. In this embodiment only the detector means 7 is rotatably mounted. Instead of one radiation means, a plurality of radiation means 54a, 54b is provided, which are preferably evenly distributed across the inner surface of the housing. Said radiation means 54a, 54b may consist of individual optical guides or individual small LED modules.

The individual LED modules 54a, 54b etc. can preferably be connected and disconnected separately since a control means preferably connects or disconnects individual light waves. In this embodiment, glass fibers are preferably used.

In another preferred embodiment it is possible to position the detector means 7, a plane element, preferably substantially along the entire guiding device 51, 52.

Additionally to the light sources 54a, 54b etc. shown in FIG. 3 another radiation source may be provided which emits diffused light. For this purpose for example frosted-glass disks, diffusor disks or the like can be used.

Figure 4:
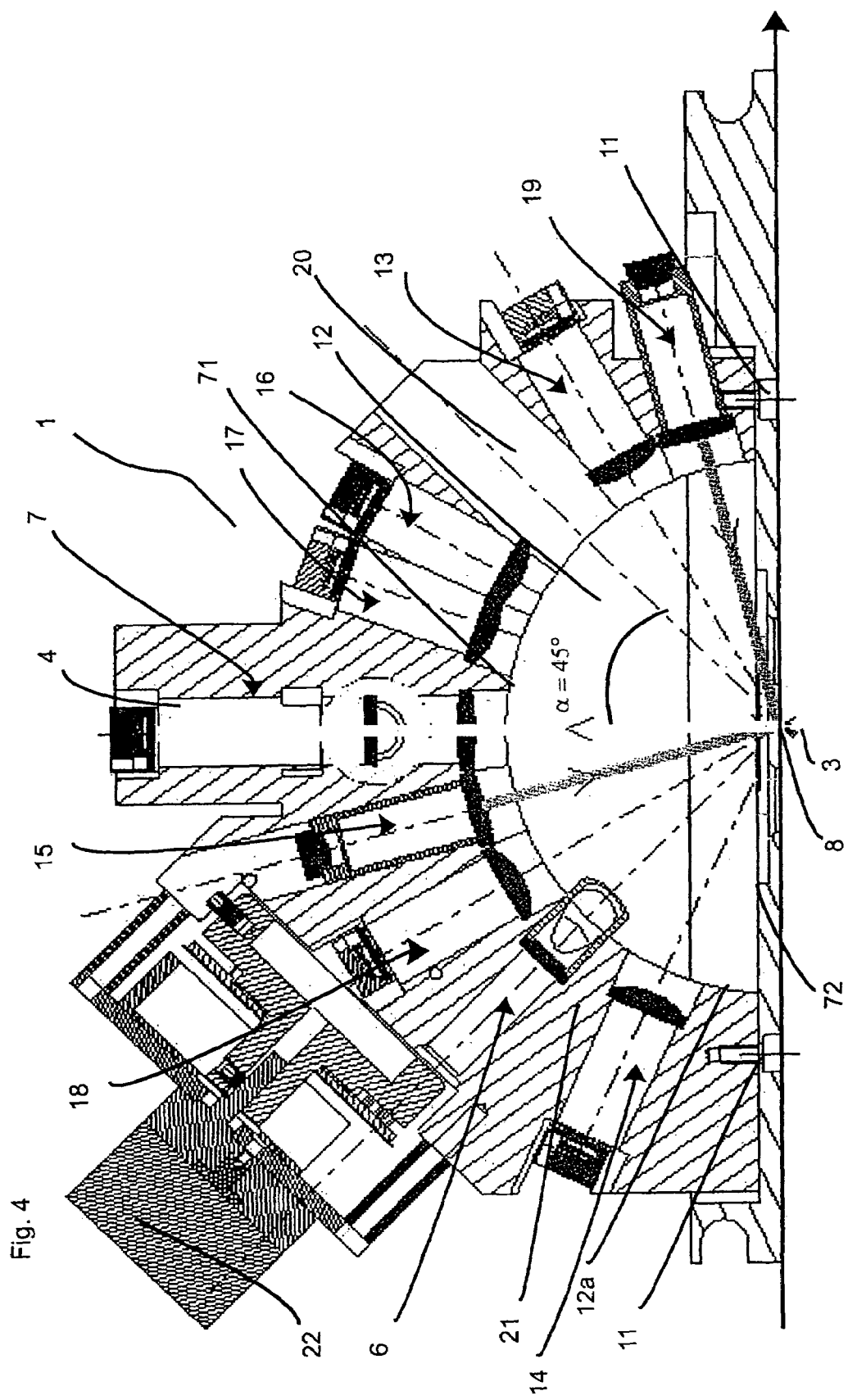
FIG. 4 is a vertical cross-section of the present device for examining surfaces.

FIG. 4 shows the device of the invention for examining optical surfaces 3. The FIGS. 4 and 5 do not illustrate guiding devices. One embodiment of the invention provides for all of the radiation and detector means to be mounted stationary, i.e. the spatial angles are not variable. Said device comprises a housing 21 including a hollow space 12 in its interior.

This hollow space 12 is configured as a semicircle or, in three-dimensional view, as a hemisphere or a hemispherical segment. However, it is also conceivable to provide other structures for said hollow space. An inner surface 71 of the hollow space exhibits radiation- or light-reflecting properties, at least in portions. As illustrated above, preferably the entire inner surface exhibits radiation- or light-reflecting properties. Preferably a bottom surface 72 also exhibits radiation- or light-reflecting properties.

The bottom surface 72 of the housing 21 comprises an aperture 8 beneath which the surface to be examined 3 is positioned. Reference numeral 15 indicates a first radiation means and reference numeral 19, a second radiation means.

Said radiation means 15, 19 emit light to the surface to be examined 3 at a predetermined spatial angle. Preferably said radiation is directional.

The first spatial subangles at which said radiation means 15 and 19 are positioned, are $\alpha=-15°$ or $\alpha=+75°$. A spatial subangle $\alpha=0°$ is understood to mean the angle at which light is directed from the surface to be examined 3 perpendicularly upwardly in FIG. 4.

In this case the angle $\beta$ which indicates the tilt of the configuration around the axis x is also 0°. The embodiment shown in FIG. 4 provides that all of the radiation means are placed on the surface 3 in a perpendicular plane running through the X tubes, i.e. the angle $\beta=0°$ for all of the radiation means. Reference numeral 7 indicates a camera and reference numeral 4, a photo sensor. These two are positioned at an angle $\alpha=\beta=0°$, i.e. they detect the light emitting from the surface to be examined perpendicularly upwardly. The arrangement of camera and detector ensures that both measuring means detect or characterize the same light.

It is also conceivable to provide, instead of two radiation means 15 and 19, only one radiation means whose spatial angles may be freely selected. The camera 7 and the photo sensor 4 may be positioned at spatial angles deviating from (0°; 0°) but possibly also at different angles.

The reference numerals 13, 14, 16, 17, and 18 indicate further photo detectors. In this provided embodiment the photo detectors are positioned at the spatial subangles $\alpha=-60°$ (photo detector 14), $\alpha=-30°$ (photo detector 18), $\alpha=20°$ (photo detector 17), $\alpha=30°$ (photo detector 16) and $\alpha=60°$ (photo detector 13). Another photo detector or another radiation means may be provided in the aperture 20.

Alternatively it is conceivable to provide, in lieu of the detectors, more radiation means or to concurrently provide radiation means and detectors at the same or adjacent locations. This may for example be realized by means of beam splitters wherein for example dichroic reflectors and the like may be used.

For example a combined radiation and detector means can be configured such that a dichroic reflector positioned at 45° relative to a geometrical connecting line between the radiation means and the incidence point of the radiation on the surface, allows incidence of light emitting from a radiation means while with respect to light reflected back from the surface to be examined it is substantially light-transmitting, substantially allowing light to pass through to a detector means.

Reference numerals 11 refer to an adjusting device which preferably serves to adjust the position of the device for examining surfaces relative to the surface to be examined. The housing section 22 may receive for example displays for the user, the control means of the individual detector means and radiation means, control means, motors and the like.

Figure 5:
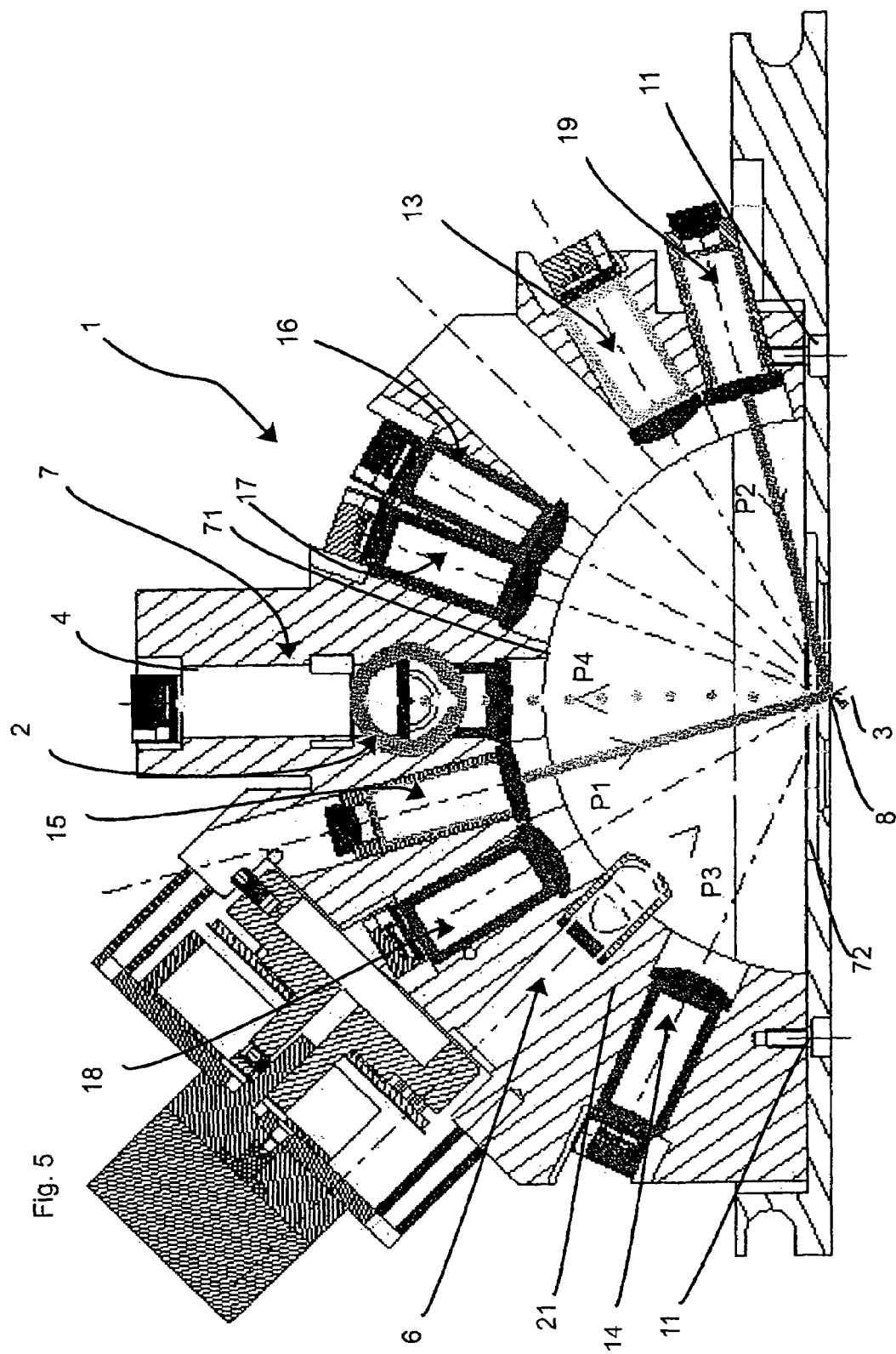
FIG. 5 is a vertical cross-section of the device similar to that shown in FIG. 4, using another measuring method.

With reference to FIG. 5 the measuring method applied with the device of the invention will now be described. The arrows P1 and P2 indicate the light emitting from the radiation sources 15 and 19 incident on the surface 3. It radiates along the arrow P4 (illustrated as a dotted line) in the direction of the camera 7. The camera 7 configuration comprises a beam splitter system illustrated in FIG. 7. Said beam splitter causes that the ray running along the arrow P4 to split, which ray is combined of a component originally emitting from the radiation means 6 along the arrow P3, and the above-mentioned rays originating from the radiation means 15 and 19.

Since the camera allows local resolution of the illustrated image, a local resolution of the surface to be examined can thus be displayed. In this way the individual pigments or flakes can be rendered visible.

Instead of the system employed herein which comprises both a camera 7 and a photo detector 4 it is also conceivable to capture the measurement only with a camera and to determine the integral intensity, in particular but not exclusively, computer-aided from the incidence image in the camera.

In this way it is possible to examine the details of the surface texture, i.e. the precise geometrical position of the pigments, on or in the individual layers of paint and thus to assess the effects resulting among other things from the density, distribution and type of the ornamental pigments used.

The light emitting from the radiation means 6 is also projected on the surface 3 where it is captured at different spatial angles. As mentioned above, the ray reflected back at (0°; 0°) is captured by the detector means 4. The illustrated embodiment further provides capturing by means of the detector means 13, 14, 16, 17 and 18 at the other spatial angles indicated above.

As mentioned above, the materials to be examined such as the finishes exhibit different optical properties depending on the direction from which they are illuminated. The individual detectors 13 to 18 will generate different spectral results since they simulate different observation angles for example of a human observer.

Another embodiment provides use of a plurality of radiation means positioned at different spatial angles which also simulate different observation angles for example by means of a stationary detector. As mentioned above, the radiation means 19 is positioned at a first spatial subangle of −75°, i.e. the light emitting from said radiation means is projected onto the surface to be examined 3 at a comparatively steep angle. This arrangement of the radiation means 19 primarily serves to examine curved, in particular concave, surfaces.

Figure 8C:
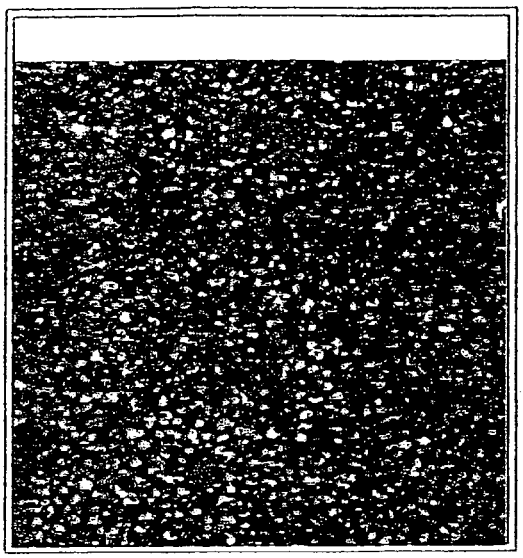
FIG. 8c is an illustration of the measuring result obtained with the device in FIG. 4.
Figure 8B:
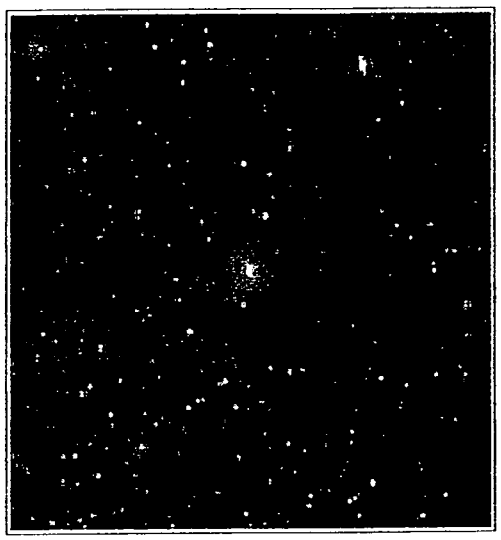
FIG. 8b is another illustration of the measuring result obtained with the device in FIG. 4.

This application is suitable for detecting pigments having high radiation intensity relative to the environment, as shown in FIG. 8*b*.

As mentioned above, the individual radiation means can be operated independently of one another. This means that it is possible to irradiate the surface only by one of the two radiation means 15 or 19 or concurrently by both. The two variants may be combined to carry out a complete measuring cycle.

For examining gloss, this embodiment irradiates the surface concurrently with the two radiation means 15 and 19 and the camera 7 captures the image.

For examining graininess, the radiation means 15 in the illustrated embodiment is set to −15° for radiating, and detecting takes place at 0°.

In addition to the illustrated radiation means, another radiation means emitting non-directional radiation may be used. In this way one can for example simulate illumination of the surface 3 on overcast days. As specified above, non-directional irradiation can be generated in particular but not exclusively through diffusor disks or individual radiation sources distributed across the space.

It is also conceivable to use directional and non-directional radiation jointly, for example consecutively or substantially concurrently.

Figure 6:
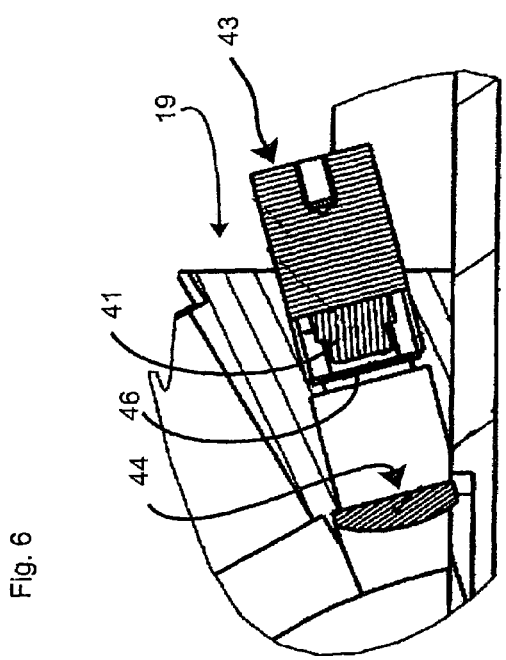
FIG. 6 is a detail view of FIG. 4.

FIG. 6 shows a detailed view of the radiation means 19. It comprises a high performance LED 41 placed in a housing 43. Furthermore an aperture 46 is provided and a lens 44 to direct collimated light at the surface. In addition to one light-emitting diode, a number of light-emitting diodes may be provided having different emission spectra in particular in visible range. Also, the individual radiation means may comprise light-emitting diodes having different emission spectra. Further, radiation means may be provided emitting substantially white light or light approximated to white light.

FIG. 7 shows a lateral cross-sectional view of the device of the invention in FIG. 4. As discussed above, all of the radiation means and detector means herein are positioned at a spatial subangle β=0°. The dashed line indicates the spatial subangle β where the device would be positioned at 45°. A preferred embodiment provides that the device can be tilted about the point P on the axis x shown in FIG. 4. In this way it is possible to radiate and to detect light substantially at any desired spatial subangle β.

As mentioned, the device of the invention comprises a beam splitter system 2 for directing at the camera the light incident on the surface in FIG. 5 along the arrows P1 and P3 and reflected back along the arrow P4. It is deflected through a beam splitter 31 substantially by 90° and guided through a filter and a lens to the camera 7 or the photosensitive surface. Another portion (not shown) of the light is guided on to the detector means 4.

Another preferred embodiment provides that the position of the camera 7 or the photosensitive surface is displaced relative to the beam S, preferably in the Z and X directions which run vertically in the drawing plane or perpendicularly in the drawing plane, respectively. It is further possible to provide at the bottom surface of the housing 43 adjusting devices (not shown) to orient the device precisely, for example perpendicularly, relative to the surface to be examined.

Figure 8A:
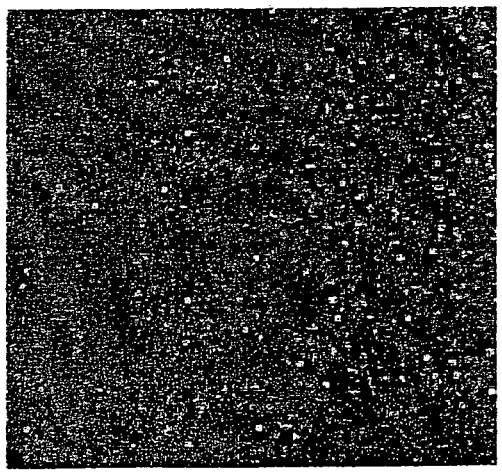
FIG. 8a is an illustration of the measuring result obtained with the device in FIG. 4.

The FIGS. 8a, 8b and 8c show examples of the surface effects which the device of the invention can capture. FIG. 8a illustrates a color shift resulting from a curved surface. Said color shift can for example be examined by means of a color picture camera. One can examine in detail which changes of the incidence and detection angle lead to which changes in color and brightness. Further embodiments provide to use, not a black-and-white camera but a color camera which provides additional information on the colors of the individual pigments. Use of a black-and-white camera and a plurality of radiation sources having different emission spectra will also provide information on the color of the pigments.

Figure 8D:
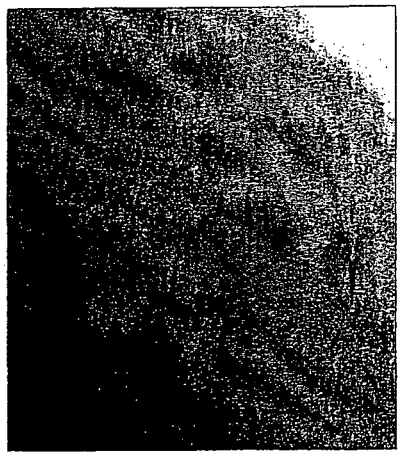

It is also apparent that this capturing arrangement allows to capture light/dark contrasts resulting from different observation angles. While the image appears somewhat darker at the top on the left, it is brighter at the bottom on the right. FIG. 8d does not show a camera-captured image of the surface but a schematic illustration of the brightness pattern illustrated in FIG. 8a. Depending on the observation angles, reflection differs greatly between the individual pigments and in this way creates the light/dark transitions illustrated.

FIG. 8b is a camera-captured measurement of the surface wherein a corresponding spatial angle, e.g. (75°, β) of the radiation means causes individual pigments or flakes to reflect particularly intensely. Such capturing allows an examination of the distribution of the individual pigments or also their sizes and reflective capabilities. For generating the captured measurement illustrated in FIG. 8b it is preferred to use an incidence or first spatial subangle α at a high value. Since the camera detects beneath 0°, the absolute majority of the light reflected off the surface does not enter the camera such that the effect of the flakes can be measured with a minimum of background illumination. The illustration of FIG. 8b shows individual pigments.

FIG. 8c illustrates the structure of the surface to be examined. In this way the graininess of the surface can be determined by radiating with diffused light or at suitable incidence angles.

It is also possible to obtain the image shown in FIG. 8c by varying the camera resolution. Another embodiment provides the use of digital filters for this purpose.

The invention claimed is:

1. A device for examining the optical properties of a surface to be examined made up of a plurality of individual pigments, the device comprising:
   at least one first radiation means emitting collimated radiation to the surface to be examined at least at a first predetermined spatial angle;
   at least one first detector means for capturing the radiation emitted to and reflected back from the surface wherein said detector means comprises an image-capturing component configured for allowing a local resolution of detected radiation and is positioned at least at a second predetermined spatial angle relative to said surface, said local resolution enabling examination of the individual points of said radiation detected by said detector means and thereby the examination of the individual pigments and the effects resulting therefrom;
   at least one further radiation means emitting non-collimated or diffused radiation simultaneously at a plurality of third spatial angles to the surface to be examined;
   wherein said first, second and third predetermined spatial angles are a tuple of a first spatial subangle and a second spatial subangle;
   wherein at least one spatial angle at which said radiation means and/or said detector means are positioned, is variable; and
   wherein the radiation means and the detector means are positioned in a substantially closed volume space which exhibits light-reflecting properties.

2. The device according to claim 1 wherein said first spatial subangle $\alpha_1$, at which said first radiation means is positioned relative to the surface to be examined, is variable.

3. The device according to claim 1 wherein said first spatial subangle $\alpha_2$, at which said first detector means is positioned relative to the surface to be examined, is variable.

4. The device according to claim 1 wherein said first spatial subangles $\alpha_1$ and/or $\alpha_2$ are variable in the range of 0° to 360°.

5. The device according to claim 1 wherein a control device is provided for actuating said at least one spatial angle in a predetermined range.

6. The device according to claim 5 wherein said control device allows incremental changes of at least one spatial angle.

7. The device according to claim 5 wherein said control device allows setting said at least one spatial angle to a predetermined value.

8. The device according to claim 1 wherein at least one radiation means and/or at least one detector means are positioned on at least one guiding device which allows changes in the position of the radiation means and/or the detector means on a predetermined path.

9. The device according to claim 8 wherein said path runs substantially in a circle around the surface to be examined.

10. The device according to claim 8 wherein said at least one guiding device is configured such that at least one of the spatial angle at which said radiation means is positioned, and the spatial angle at which said detector means is positioned, can substantially be changed independently of one another.

11. The device according to claim 8, wherein motor means are provided to allow motor-aided shifting of at least one of said radiation means and said detector means on said at least one guiding device or to allow a rotation.

12. The device according to claim 1 wherein at least one further detector means is provided which detects radiation emitted to and reflected back from said surface.

13. The device according to claim 1, wherein said first detector means further comprises means for determining the total intensity of incident radiation.

14. The device according to claim 13, wherein said first detector means is a CCD chip and the determination of said total intensity is achieved though integration of the incidence intensities on the individual photo cells of said CCD chip.

15. The device according to claim 1, wherein said first detector means is a color picture camera which determines a color shift resulting from a curved surface to be examined.

16. The device according to claim 15, wherein said color picture camera provides additional information on the colors of said individual pigments.

17. The device according to claim 1, wherein said first radiation means and said further radiation means permit a concurrent radiation of the surface, at least intermittently.

18. The device according to claim 1, wherein said first radiation means and said further radiation means are operated independently of one another to irradiate the surface by at least one of said first radiation means and said further radiation means.

19. The device according to claim 18, wherein control means are provided for actuating said first radiation means and said further radiation means.

20. A device for examining the optical properties of a surface to be examined made up of a plurality of individual pigments, the device including:
    at least one first radiation means emitting radiation at least at a first predetermined spatial angle to the surface to be examined;
    at least one first detector means for capturing the radiation emitted to and reflected back from the surface wherein said first detector means, allowing a local resolution of detected radiation, is positioned at least at a second predetermined spatial angle relative to said surface, said local resolution enabling examination of the individual points of said radiation detected by said detector means and thereby the examination of the individual pigments and wherein said detector means is selected from a group including cameras and CCD chips; and
    at least one further detector means detects radiation emitted to and reflected back from the surface and which only permits an examination of the radiation intensity and the spectral characteristics without local resolution;
    wherein said first and second predetermined spatial angles are a tupel of a first spatial subangle and a second spatial subangle;
    wherein the radiation means and the detector means are positioned in a substantially closed volume space which exhibits light-reflecting properties.

21. The device according to claim 20 wherein said at least one spatial angle, at which said further detector means is positioned, is variable.

22. The device according to claim 20 wherein said surface is irradiated concurrently with at least two said radiation means at least intermittently.

23. The device according to claim 20 wherein said further detector means is selected from a group of detector means including photo cells, photo elements and photo diodes.

24. The device according to claim 20 wherein said first detector means is positioned above the surface at a first spatial subangle of substantially 0°.

25. The device according to claim 24 wherein at least one further detector means is positioned relative to the surface at a first spatial subangle whose amount is larger than 70°.

26. The device according to claim 20 wherein said at least one radiation means is positioned relative to the surface at a first spatial subangle selected from a group of angles including −45° and 75°.

27. The device according to claim 20 wherein said at least one radiation means is positioned relative to the surface at a first spatial subangle whose amount is larger than 70°.

28. The device according to claim 20 wherein at least two of said further detector means are positioned relative to the surface at a first spatial subangle selected from a group of angles including −75°, −15°, 25°, 45°, 75° and 110°.

29. The device according to claim 20 wherein said at least one radiation means emits directional radiation.

30. The device according to claim 20 wherein said at least one radiation means emits non-directional radiation.

31. The device according to claim 20 wherein both said radiation means and said detector means are substantially positioned at the same second spatial subangle.

32. The device according to claim 20 wherein both said radiation means and said detector means are substantially positioned on an arc of a circle.

33. The device according to claim 20 wherein means are provided such that both a first said detector means and a second said detector means can detect radiation at the same predetermined spatial angle.

34. The device according to claim 33, wherein said means is a beam splitter that causes a specified portion of the reflected rotation to reach said first detector means and another portion to reach said further detector means.

35. The device according to claim 34, wherein said beam splitter is a partly silver reflector.

36. The device according to claim 20, wherein said first detector means is a camera and said further detector means is a photo detector.

37. The device according to claim 20, wherein said first detector means is a color picture camera that determines a color shift resulting from a curved surface to be examined.

38. The device according to claim 37, wherein said color picture camera provides additional information on the colors of said individual pigments.

39. The device according to claim 20, wherein said first detector means is a CCD chip and said further detector means determines the total intensity of the reflected radiation.

* * * * *